United States Patent [19]
Barouk

[11] Patent Number: 4,969,909
[45] Date of Patent: Nov. 13, 1990

[54] ARTICULAR PROSTHETIC IMPLANT WITH TEMPORARY FIXING MEANS

[76] Inventor: Louis S. Barouk, La Manchotte - Yvrac - 33370, Tresses, France

[21] Appl. No.: 263,328

[22] Filed: Oct. 27, 1988

[30] Foreign Application Priority Data

Oct. 27, 1987 [FR] France .................. 87 15024

[51] Int. Cl.$^5$ .............................................. A61F 2/42
[52] U.S. Cl. .......................................... 623/21; 623/22; 623/23; 606/62
[58] Field of Search ............................ 623/21, 22, 23; 128/92 YD, 92 YE, 92 YF; 606/54, 55, 59, 60, 61, 62

[56] References Cited

U.S. PATENT DOCUMENTS

| | | | |
|---|---|---|---|
| 2,579,968 | 12/1951 | Rush | 606/62 |
| 3,641,590 | 2/1972 | Michele | 623/22 |
| 3,809,075 | 5/1974 | Matles | |
| 4,224,699 | 9/1980 | Weber | 623/23 |
| 4,385,404 | 5/1983 | Sully et al. | |

FOREIGN PATENT DOCUMENTS

| | | | |
|---|---|---|---|
| 0013863 | 8/1980 | European Pat. Off. | 623/22 |
| 3535959 | 4/1987 | Fed. Rep. of Germany | 623/22 |
| 1109143 | 8/1984 | U.S.S.R. | 128/92 YF |

*Primary Examiner*—Randall L. Green
*Assistant Examiner*—Stephanie L. Iantorno
*Attorney, Agent, or Firm*—Foley, Lardner, Schwartz, Jeffery, Schwaaab, Mack, Blumenthal & Evans

[57] ABSTRACT

The invention provides an articular prosthetic implant with temporary fixing, more particularly intended for the feet and the hands, characterized in that it is formed, on the one hand, of a cup or similar, shape formed centrally with a hole (2) and intended to be positioned between two bone pieces (4,5) in line with their articulation and, on the other hand, a reovable fixing pin (3) able to slide freely in the hole (2) in said cup (1), for temporarily immobilizing the cup (1) and the adjacent bone pieces (4,5) by being inserted through the medullary canals of the bone pieces concerned (4,5,6) and the hole (2) in the previously positioned cup (1).

17 Claims, 1 Drawing Sheet

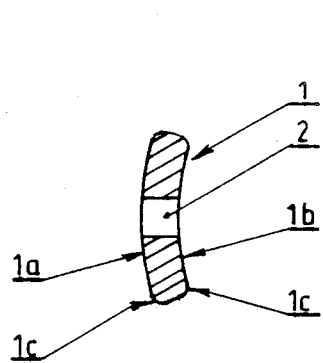
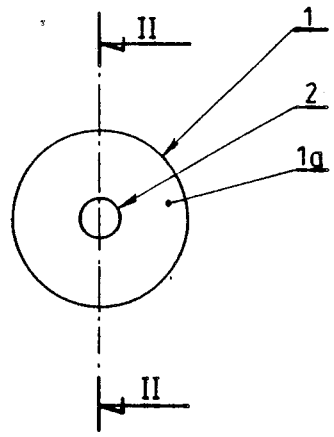
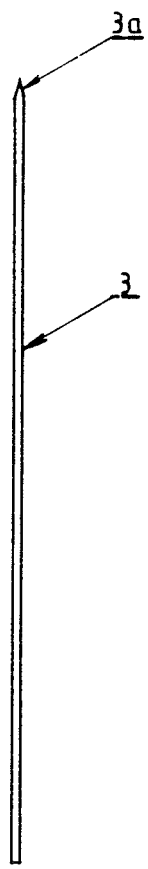
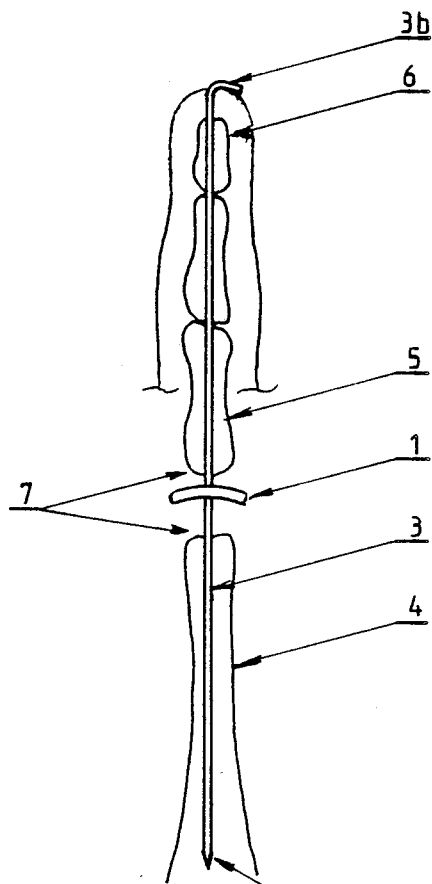

ARTICULAR PROSTHETIC IMPLANT WITH TEMPORARY FIXING MEANS

The present invention relates to an articular prosthetic implant for orthopaedic surgery.

Numerous articular prosthetic implants are already used in orthopaedic surgery for replacing the damaged articular surfaces. They are generally formed of one or two prosthetic parts positioned between two pieces which are to remain mobile with respect to each other.

These two prosthetic parts are fixed to the bone pieces definitely by means of rods or roughnesses on each of these two prosthetic parts and penetrating into one of the two bone pieces, or both, with or without the intermediary of a surgical cement, e.g. methyl methylacrylate or any other fixing method.

The purpose of the invention is to provide in the case of phalangeal metatarsal or metacarpal articular prostheses a new technique for fixing such prosthetic implants providing both strict positioning of the implant and the absence of final prosthetic anchorage in the bone pieces.

For this, the invention provides an articular prosthetic implant with temporary fixing, more particularly intended for the feet and the hands, characterized in that it is formed, on the one hand, of a cup or similar shape, formed centrally with a hole and intended to be positioned between two bone pieces in line with their articulation and, on the other hand, a removable fixing pin able to slide freely in the hole in said cup, for temporarily immobilizing the cup and the adjacent bone pieces by being inserted through the medullary canals of the bone pieces concerned and the hole in the previously positioned cup.

Such a device provides perfect centring of the cup with respect to the adjacent bone pieces for the time required for reconstituting the peri-prosthetic fibrous tissues (generally four weeks) and makes it possible, after this time, to readily withdraw the immobilizing pin without surgical operation.

The cup thus finds its freedom of movement again with respect to the opposing bone pieces while remaining held perfectly in position.

Other features and advantages will be clear from the following description of one embodiment of the invention, given solely by way of example with reference to the accompanying drawings in which:

FIG. 1 shows a front elevational view of a cup prosthesis in accordance with the invention;

FIG. 2 is an axial cross sectional view through line II—II of the cup of FIG. 1;

FIG. 3 is an elevational view of the pin of the invention; and

FIG. 4 illustrates the cup and its immobilizing pin in position in a toe.

In FIGS. 1 and 2 an implant of the invention has been shown formed of a circular cup 1 preferably with parallel respectively convex 1a and concave 1b faces, made from a material tolerated by living tissues, e.g. stainless steel, titanium, ceramic etc. . . The diameter of cup 1 may of course vary depending on the phalangeal metatarsal or metacarpal articulations, e.g. between 8 and 18 mm in most cases.

The thickness of cup 1 is relatively large, about 2 to 5 mm. The curvature of faces 1a and 1b is slight and corresponds substantially to that of the contacting articular surfaces.

The circular peripheral edges 1c are slightly blunted.

The cup is formed axially at its centre with a hole 2 of a diameter of about one millimeter or slightly more, so as to allow a temporary fixing pin, illustrated at 3 in FIG. 3, to pass freely therethrough.

The pin 3 is cylindrical, of a diameter slightly less than that of hole 2 in cup 1 and made preferably from a material such as stainless steel which can be bent and cut to the desired length.

In FIG. 4, a toe has been shown having an implant of the invention. Cup 1 is interposed between the metatarsus 4 and the first phalanx 5 and is held in position by pin 3 engaged through the medullary canal of the three phalanxes and of the metatarsus, end 3a being inserted into the distal bony portion of the metatarsus 4.

The other end of pin 3 projects from the end of the last phalanx 6 and is bent at 3b against the end of said phalanx.

Positioning of the assembly is as follows.

The articulation to be treated is incised and cleaned. In this connection, if required, as shown in FIG. 4 at 7, the damaged facing bone pieces may be removed. Pin 3 is then inserted into the medullary canal of the successive phalanxes, towards the distal portion of the toe; the pin then comes out at the end of the toe. Then, the pin is directed towards the proximal portion, successively inserted through the central hole 2 of cup 1 and, finally, into the medullary canal of the metatarsus 4. The pin is then sectioned at its distal end so as to leave projecting from the toe a small length of pin which will be bent back so as to form end 3b.

Such immobilization by fixing the cup 1 makes it possible, as can be seen in FIG. 4, to perfectly position the cup both in the axis of the bone pieces concerned 4 and 5 and at the desired distance with respect to the facing ends of said bone pieces, so as to leave room for regeneration both of the bone tissues and of the fibrose for maintaining cup 1 in position and a good friction surface with respect to the latter.

Pin 3 is left in position for the time required for the regeneration of the tissues surrounding the cup, e.g. a month, then removed very easily by pulling on the curved end 3b without having to intervene surgically. The withdrawn pin leaves cup 1 interposed in the correct position between the two adjacent bone pieces without risk of loosening or bone erosion which can be seen in known prostheses.

The articulation thus equipped recovers complete mobility since no fixing or hindrance exists between cup 1 and the two adjacent bone pieces.

Finally, the invention is obviously not limited to the embodiment shown and described above but covers on the contrary all variants thereof particularly in so far as the shapes and dimensions of cup 1 and pin 3 are concerned, as well as the nature of the material forming these latter.

Thus, the faces 1a and 1b of cup 1 are preferably parallel but they could have slightly different curvatures.

Similarly, the implant of the invention may be positioned in line with any one of the articulations of a finger or toe, even several articulations of the same finger or toe.

I claim:

1. Phalangeal metatarsal or metacarpal articular prosthetic implant, the implant being temporarily fixable to at least one bone piece, comprising a generally cup shaped member formed with a hole substantially through a central portion thereof, said member being adapted to be positioned between two bone pieces in line with their articulation, and a removable fixing pin arranged to slide freely in the hole in said member for temporarily immobilizing said member and the adjacent bone pieces by being inserted through the medullary canals of the bone pieces and the hole in said member.

2. Implant according to claim 1, wherein said member comprises substantially parallel faces, one said face being convex while the other is concave.

3. The implant according to claim 2, wherein said faces contact adjacent articular surfaces of said bone pieces and said faces have a slight curvature substantially corresponding to a curvature of said adjacent articular surfaces.

4. The implant according to claim 2, wherein said faces are between about 2 mm and about 5 mm apart.

5. The implant according to claim 1, wherein the generally cup shaped member comprises a material tolerated by living tissue.

6. The implant according to claim 1, wherein the cup shaped member has a diameter adapted to said articulations.

7. The implant according to claim 6, wherein said generally cup shaped member has a diameter of between about 8 mm and 18 mm.

8. The implant according to claim 1, wherein said hole has a diameter of approximately 1 mm and said pin has a diameter slightly less than said hole diameter.

9. The implant according to claim 1, wherein said pin comprises a material which can be bent and cut to a desired length.

10. The implant according to claim 1, wherein said pin is comprised of stainless steel.

11. The implant according to claim 1, wherein said removable fixing pin has a first and second end, one of the ends inserted through the medullary canal of the bone pieces and the hole in the member and the other end projecting outwardly from one of the bone pieces to facilitate removal of the pin.

12. A method of implanting a phalangeal metatarsel or metacarpal prosthetic device in a digit comprising:
   (a) locating a generally cup-shaped member between a proximal bone piece and a distal bone piece in line with their articulation, the member having a hole substantially in a central portion of the cup;
   (b) inserting a first end of a pin through a medullary canal of the distal bone piece and a medullary canal of at least one adjacent phalanx of the digit, toward a tip of the digit;
   (c) causing the first end of the pin to protrude from the tip forming a projection;
   (d) directing a second end of the pin into and through the hole in the member; and
   (e) inserting the second end into the medullary canal of the proximal bone piece.

13. The method of claim 12 further comprising: bending said projection to form an end piece.

14. The method of claim 12 further comprising removing the pin after regeneration of tissues surrounding the cup-shaped member.

15. A method of implanting a phalangeal metatarsal or metacarpal prosthetic device in a digit comprising:
   (a) inserting a first end of a pin through a medullary canal of a first bone piece, and a medullary canal of at least one adjacent distal phalanx of the digit, toward a tip of the digit;
   (b) then causing the first end of the pin to protrude from the tip forming a projection;
   (c) subsequently locating a generally cup-shaped member between the first bone piece and a second bone piece, the second bone piece being adjacent to the first and located in a proximal portion of the digit, the cup-shaped member being located in line with the articulation of the bone pieces, the member having a hole substantially in a central portion of the cup;
   (d) directing a second end of the pin into and through the hole in the member; and
   (e) inserting the second end into a medullary canal of the second bone piece.

16. The method of claim 15 further comprising: bending said projection to form an end piece.

17. The method of claim 15 further comprising removing the pin after regeneration of tissues surrounding the cup-shaped member.

* * * * *